US008420386B2

(12) United States Patent
Ivics et al.

(10) Patent No.: US 8,420,386 B2
(45) Date of Patent: Apr. 16, 2013

(54) TRANSPOSON-BASED TARGETING SYSTEM (75) Inventors: Zoltan Ivics, Berlin (DE); Zsuzsanna Izsvak, Berlin (DE)

(73) Assignee: Max-Delbruck-Centrum fur Molekulare Medizin (MDC), Berlin (DE)

( * ) Notice: Subject to any disclaimer, the term of this patent is extended or adjusted under 35 U.S.C. 154(b) by 1033 days.

(21) Appl. No.: 10/544,971

(22) PCT Filed: Feb. 10, 2004

(86) PCT No.: PCT/EP2004/001221
§ 371 (c)(1),
(2), (4) Date: Jun. 16, 2006

(87) PCT Pub. No.: WO2004/070042
PCT Pub. Date: Aug. 19, 2004

(65) Prior Publication Data
US 2006/0258603 A1    Nov. 16, 2006

(30) Foreign Application Priority Data
Feb. 10, 2003   (EP) .................................... 03002638

(51) Int. Cl.
*C12N 15/00*   (2006.01)
*C12N 15/87*   (2006.01)
*C12N 15/64*   (2006.01)
*A61K 48/00*   (2006.01)

(52) U.S. Cl.
USPC ....... 435/320.1; 435/466; 435/91.4; 514/44 R (58) Field of Classification Search ........................ None
See application file for complete search history.

(56) References Cited

U.S. PATENT DOCUMENTS

| 5,736,387 | A  | * | 4/1998  | Paul et al. ................. 435/320.1 |
| 5,958,775 | A  |   | 9/1999  | Wickstrom et al. ........... 435/455 |
| 6,489,458 | B2 |   | 12/2002 | Hackett et al. ............... 536/23.2 |
| 7,431,922 | B2 | * | 10/2008 | Song et al. ................. 424/93.21 |
| 2003/0134350 | A1 |   | 7/2003  | Sera |
| 2006/0210977 | A1 | * | 9/2006  | Kaminski ........................ 435/6 |
| 2006/0236413 | A1 | * | 10/2006 | Ivics et al. ..................... 800/14 |

FOREIGN PATENT DOCUMENTS

| WO | WO98/40510  |    | 9/1998 |
| WO | WO01/30965  | A2 | 5/2001 |

OTHER PUBLICATIONS

Hughes, K.T., et al., Transitory CIS Complementation a Method for Providing Transposition Functions to Defective Transposons, Genetics, 119:9-12 (1988).
Izsvak, Z., et al., Healing the Wounds Inflicted by Sleeping Beauty Transposition by Double-Strand Break Repair in Mammalian Somatic Cells, Molecular Cell, 13:279-290 (2004).
Izsvak, Z., et al., Sleeping Beauty, a Wide Host-Range Transposon Vector for Genetic Transformation in Vertebrates, J. Mol. Biol. 302:93-102.(2000).
Kaminski, J.M., et al., Design of a Nonviral Vector for Site-Selective, Efficient Integration into the Human Genome, FASEB J. 16:1242-1247 (2002).
Ivics, Z., et al., Targeted Sleeping Beauty Transposition in Human Cells, Molecular Therapy, 2007, 15(6):1137-1144.
Wilson, M.H., et al., Functional Zinc Finger/Sleeping Beauty Transposase Chimeras Exhibit Attenuated Overpopulation Inhibition, FEBS Letters, 2005, 579:6205-6209.

* cited by examiner

*Primary Examiner* — Doug Schultz
(74) *Attorney, Agent, or Firm* — Pillsbury Winthrop Shaw Pittman LLP (57) ABSTRACT

The present invention relates to a targeting system comprising, preferably as distinct components (a) a transposon which is devoid of polynucleotide encoding a functional transposase comprising (aa) a polynucleotide of interest and; (ab) a DNA sequence specifically recognized by a DNA binding domain; and (ba) a fusion protein comprising (i) said DNA binding domain; or (ii) a (poly)peptide binding domain binding to a (poly)peptide comprising said DNA binding domain; and (iii) a DNA targeting domain; or (iv) a (poly)peptide binding domain that binds to a cellular or engineered (poly)peptide that comprises a DNA targeting domain; or (bb) a polynucleotide encoding the fusion protein of (ba); and (ca) a transposase or a fragment or derivative thereof having transposase function; or (cb) a polynucleotide encoding the transposase or fragment or derivative thereof having transposase function of (ca).

20 Claims, 7 Drawing Sheets

TRANSPOSON-BASED TARGETING SYSTEM

The present invention relates to a targeting system comprising, preferably as distinct components (a) a transposon which is devoid of a polynucleotide encoding a functional transposase comprising (aa) a polynucleotide of interest and; and (ab) a DNA sequence specifically recognized by a DNA binding domain; and (ba) a fusion protein comprising (i) said DNA binding domain; or (ii) a (poly)peptide binding domain binding to a (poly)peptide comprising said DNA binding domain; and (iii) a DNA targeting domain; or (iv) a (poly)peptide binding domain that binds to a cellular or engineered (poly)peptide that comprises a DNA targeting domain; or (bb) a polynucleotide encoding the fusion protein of (ba); and (ca) a transposase or a fragment or derivative thereof having transposase function; or (cb) a polynucleotide encoding the transposase or fragment or derivative thereof having transposase function of (ca).

In the specification a number of documents is cited. The disclosure content of these documents including manufacturers' manuals is herewith incorporated by reference.

DNA transposition requires two main functional components of the transposon system: the transposase protein and the transposase binding sites within the terminal inverted repeats of the transposon. Transposition of many transposable elements, including Sleeping Beauty (SB), can occur at many sites in genomes, and target selection is believed to be mediated primarily by the transposase. A requirement for site-specific integration is to direct the transpositional complex to certain chromosomal regions or sites by specific DNA-protein interactions. Because the transposon system consists of two main functional components: the transposon DNA and the transposase protein, tethering the transpositional complex to a given site in the genome can be brought about by interactions with either of these two components.

There have been considerations in the art how to make use of transposon-based mechanisms for the sequence-specific insertion of DNA for gene therapy purposes.

Thus, Kaminski and colleagues have devised a model of using a chimeric transposase consisting of a transposase portion and a host DNA binding domain to bypass the potential requirement of host DNA-binding factors for site-selective integration (Kaminiski et al., FASEB J. 16 (2002), 1242-1247). However, following the suggestions made by Kaminski's group would not yield a useful result. This is because the direct fusion of a transposase to a host DNA binding domain would disrupt the transposase activity and thus preclude the desired targeted insertion (see Reference example 1). In addition, the model system discussed by Kaminski and colleagues relies on the transposase encoding gene still being part of the transposon. The drawback of this approach is that even if a targeted insertion would occur (which is not the case, see above) the presence of the transposase encoding gene in the integrated transposon would sooner or later lead to the transposition of the transposable element into a different chromosomal site. This is, however, an inappropriate starting point for a gene therapy approach. Therefore, the technical problem underlying the present invention was to design a transposon-based targeting system for the site-specific targeting of desired polynucleotides into DNA sequences of choice that may also be useful in gene therapy. The solution to this technical problem is achieved by providing the embodiments characterized in the claims.

Accordingly, the present invention relates to a targeting system comprising (a) a transposon which is devoid of a polynucleotide encoding a functional transposase comprising (aa) a polynucleotide of interest and; and (ab) a DNA sequence specifically recognized by a DNA binding domain; and (ba) a fusion protein comprising (i) said DNA binding domain; or (ii) a (poly)peptide binding domain binding to a (poly)peptide comprising said DNA binding domain; and (iii) a DNA targeting domain; or (iv) a (poly)peptide binding domain that binds to a cellular or engineered (poly)peptide that comprises a DNA targeting domain; or (bb) a polynucleotide encoding the fusion protein of (ba); and (ca) a transposase or a fragment or derivative thereof having transposase function; or (cb) a polynucleotide encoding the transposase or fragment or derivative thereof having transposase function of (ca).

The term "targeting system" means, in accordance with the present invention, a system comprised of (different) DNA molecule(s) or (poly)peptides that mediates a non-random, targeted integration of a transposon as defined above into a target DNA sequence. This system comprises at least the preferably three distinct molecules described herein above under (a), (ba)/(bb) and (ca)/(cb). These molecules functionally interact with each other and with a target DNA sequence whereby integration of the transposon into the target DNA sequence is achieved. This principle underlying the present invention is described in more detail further below.

The components (a) and (ba) or (bb) and (ca) or (cb) are preferably present in the targeting system as distinct components. It is further preferred in some cases that at least the transposon is retained as a distinct component. The term "distinct components" refers to the fact that the components, i.e. the transposon, polynucleotides and/or (poly)peptides recited in the targeting system of the invention may be physically distinct molecular entities. For example, in one embodiment the transposon recited in (a) and the polynucleotides recited in (bb) and (cb) do not form one single polynucleotide but are present as three distinct polynucleotides that are, optionally separately propagated, in the targeting system of the invention. On the other hand, the two polynucleotides/DNA sequences recited in (aa) and (ab) may be both parts of the distinct component (a) and thus physically linked. In further embodiments, the DNA sequence (ab) specifically recognized by a first DNA binding domain may be part of or identical with the polynucleotide of interest (aa).

The term "transposon which is devoid of a polynucleotide encoding a functional transposase" refers to a transposon based DNA molecule no longer comprising the complete sequence encoding a functional, preferably a naturally occurring transposase. Preferably, the complete sequence encoding a functional, preferably a naturally occurring transposase or a portion thereof is deleted from the transposon. Alternatively, the gene encoding the transposase is mutated such that a naturally occurring transposase or a fragment or derivative thereof having the function of a transposase, i.e. mediating the insertion of a transposon into a DNA target site is no longer contained. Alternatively, the activity is significantly reduced such as to at least 50%, better at least 80%, 90%, 95% or 99%. Mutation as referred to above includes substitution, duplication, inversion, deletion etc. as described in standard textbooks of molecular biology such as "Molecular Biology of the Gene" (eds. Watson et al.,) 4th edition, The Benjamin/Cummings Publishing Company, Inc., Menlo Park, Calif., 1987.

The transposon must retain sequences that are required for mobilization by the transposase provided in trans. These are the terminal inverted repeats containing the binding sites for the transposase. The transposon may be derived from a bacterial or a eukaryotic transposon wherein the latter is preferred. Further, the transposon may be derived from a class I or class II transposon. Class II or DNA-mediated transposable elements are preferred for gene transfer applications, because transposition of these elements does not involve a reverse transcription step (involved in transposition of Class I or retroelements) which can introduce undesired mutations into transgenes (Miller, A. D. (1997). Development and applications of retroviral vectors in Retroviruses (eds. Coffin, J. M., Hughes, S. H. & Varmus, H. E.) 843 pp. (Cold Spring Harbor Laboratory Press, New York,); Verma, I. M. and Somia, N. (1997). Gene therapy? promises, problems and prospects. Nature 389, 239-242.)

The term "polynucleotide" in accordance with the invention refers to any type of polynucleotide including RNA, DNA or PNA or modifications thereof. Preferred in accordance with the invention is that said term denotes DNA molecules.

The term "specifically recognized" means, in accordance with the present invention that the DNA binding domain recognizes and binds under physiological conditions such as occurring inside a cell only the specified DNA sequences but no undesired or essentially no undesired DNA sequences within the cell (this is preferably also true for targeting). For example, in the human genome, a stretch of 15 nucleotides, preferably of 18 nucleotides or more would normally secure that the corresponding sequence is unique. Such unique sequences can be identified and produced by the skilled person on the basis of the knowledge of the human genome and using appropriate computer programs without further ado. Similarly, whenever binding (to DNA or to (poly)peptides) is referred to, it is meant that said binding is specific. Specific binding/recognition can be assessed for, e.g. by using competition binding assays that are well known in the art.

The term "fragment or derivative" of a transposase "having transposase function" refers to fragments derived from naturally occurring transposases which lack amino acids preferably within the naturally occurring transposase and which still mediate DNA insertion. Alternatively, this term refers to derivatives of naturally occurring transposases such as fusion proteins comprising naturally occurring transposases or naturally occurring transposases, preferably joined to the fusion partner via a linker, wherein one or more amino acids have been exchanged, deleted, added, or less preferred, where inversions or duplications have occurred. Such modifications are preferably effected by recombinant DNA technology. Further modifications may also be effected by applying chemical alterations to the transposase protein. Said protein (as well as fragments or derivatives thereof) may be recombinantly produced and yet may retain identical or essentially identical features as the naturally occurring protein.

The term "(poly)peptide" refers alternatively to peptides or to polypeptides. Peptides conventionally are amino acid sequences having up to 30 amino acid whereas polypeptides (also referred to as "proteins") comprise stretches of at least 31 amino acids.

The term "DNA binding domain" refers, in accordance with the present invention, to a domain of a (poly)peptide that is capable of specifically binding to a DNA region but is not involved in mediating integration of a transposon into said DNA region. The specificity of binding occurs by interactions between amino acid residues of the DNA binding domain and specific base pairs of the DNA helix.

The term "(poly)peptide binding domain" refers, in accordance with the present invention, to a domain of a (poly)peptide that is capable of specifically binding to a second (poly)peptide. Protein-protein interactions are widely recognized in the art. They may be exerted as "key-and-lock" interactions such as occurs between antibodies and fitting antigens, biotin and avidin or enzymes and substrates. Other examples of protein-protein interactions include binding of members of a protein cascade such as a signal transduction cascade. Protein-protein interactions may be assessed using, for example, the two- or three hybrid system originally established by Fields and Song: A novel genetic system to detect protein-protein interactions. Nature. Jul. 20, 1989;340(6230):245-6; see also Topcu and Borden, Pharm. Res. 17 (2000), 1049-1055, Zhang et al., Meth. Enzymol. 306 (1999), 93-113, Fields and Sternglanz, Trends Genet. 10 (1994), 286-292. On the basis of this general knowledge, (poly)peptide binding domains may be selected or devised and subsequently employed in the targeting system of the present invention.

The term "DNA targeting domain" refers, in accordance with the present invention, to a domain of a (poly)peptide that is capable of specifically binding to a DNA region (including chromosomal regions of higher order structure such as repetitive regions in the nucleus) and is, directly or indirectly, involved in mediating integration of a transposon into said DNA region. The DNA region would preferably be defined by a nucleotide sequence which is unique within the respective genome.

The various binding domains referred to above may be part of a larger (poly)peptide that forms part of the fusion protein.

The term "engineered (poly)peptide" refers to a non-naturally occurring (poly)peptide having the above recited function. The (poly)peptide may have a basis of a naturally occurring (poly)peptide but may have been engineered to display a higher or lower specificity in DNA binding (depending on the actual purpose of the DNA targeting), a higher or lower half-life in a cellular environment etc. It may also have advantages as regards mode of recombinant production, e.g. it may be produced at lower cost as compared to its natural counterpart. The (poly)peptide may also be made up of modules derived from different proteins that, in conjunction, fulfil the above recited function.

A "cellular (poly)peptide" is a (poly)peptide that occurs within a cell and may be identical to a naturally occurring protein. In certain embodiments, it may be recombinantly produced inside the cell or introduced into the cell.

The "(poly)peptide comprising said first DNA binding domain" may also be a cellular or engineered (poly)peptide.

Figure 1A:
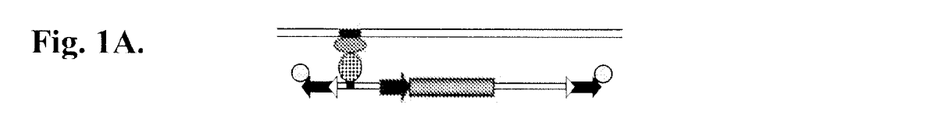
Figure 1B:
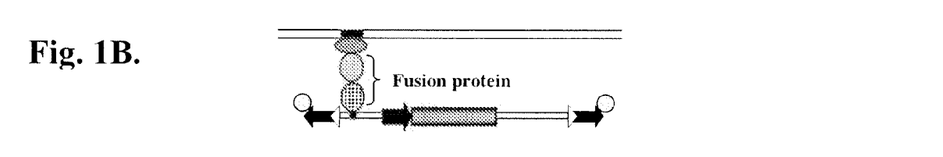
Figure 1C:
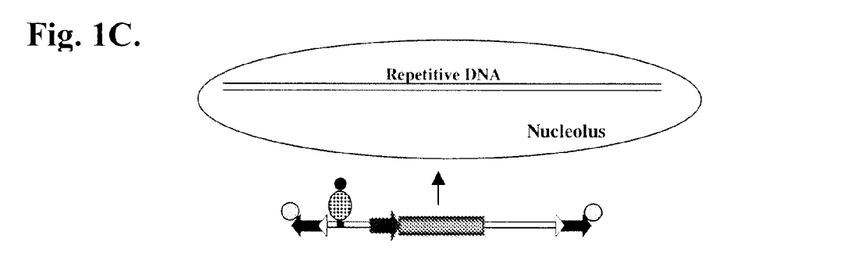

In accordance with the present invention and to achieve targeted transposition of transposons in host cells such as vertebrate cells, the following distinct experimental strategies were devised which all fall under the general principle of the present invention as described herein above. These strategies are schematically depicted in FIG. 1: 1) design of a targeting fusion protein in which one fusion partner binds to a site within the transposable element or makes contacts with a DNA-binding protein that, in turn, binds to a site within the transposable element, whereas the other partner binds to chromosomal DNA (FIG. 1A); 2) design of a targeting fusion protein in which one fusion partner makes contacts with a DNA-targeting protein (either endogenous or engineered) through protein-protein interactions, whereas the other partner is a domain or (poly)peptide that binds to a site within the transposable element, or is a domain or (poly)peptide that makes contact with a DNA-binding protein through protein-protein interactions that, in turn, binds to a site within the transposable element (FIG. 1B). A third option is that either of the above types of constructs binds to chromosomal regions of higher order structure as defined herein such as to repetitive regions in the nucleolus (FIG. 1C)

In accordance with the present invention, different combinations of compounds may be employed to successfully target DNA regions or sites of choice. These compounds may be combined prior to insertion into a cell or may be inserted molecule by molecule into the cell. Their construction allows the functional interaction with each other and with the target DNA. The invention also encompasses embodiments wherein at least one of the components of the targeting system has already been inserted into the cell and the remainder of the components still needs to be inserted. The selection of components provided by the targeting system of the present invention for the first time allows a reliable, targeted insertion of a polynucleotide of interest in a transposon-based system into a chosen DNA sequence, composition or region. The DNA region may, for example, be a region on an extrachromosomal element or a site on a chromosome such as a chromosomal gene. The design of a fusion protein allows tethering on the transposon on the one hand, either by direct binding to the transposon DNA or via an intermediate protein and targeting a DNA region of choice by means of a DNA targeting domain or, in the alternative, via an intermediate protein that contains the DNA targeting domain. Binding directly to the transposon DNA and not to a plasmid DNA as described in Kaminski et al, loc. cit., secures that the transposon, upon excision from the vector/plasmid, sequences can still be targeted to the desired DNA location and does not freely float inside the cell. This constitutes a significant advantage over the model system described by Kaminski and colleagues.

The various components of the targeting system of the present invention may be introduced into a cell as (poly) peptides or as nucleic acid molecules encoding said (poly) peptides. Introduction of (poly)peptides into the cell may have advantages in gene therapy approaches. For example, stable insertion of a transposase gene into the human genome would pose a risk of further, uncontrolled transposition events, potentially leading to insertional inactivation of essential genes, or misexpression of proto-oncogenes, leading to cancer.

Irrespective of the actual composition of the targeting system as being of proteinaceous matter or polynucleotidic matter, it is required that the polynucleotides encoding the above mentioned (poly)peptides or domains are indeed expressed in the respective host cell or host.

In a preferred embodiment of the targeting system of the invention, the polynucleotide of (bb) further encodes at least one (poly)peptide as described in (ii) or (iv).

In this embodiment of the invention, at least one of the intermediate or "bridging" (poly)peptides contacting the DNA via their DNA binding or targeting domain is also encoded by the polynucleotide encoding the fusion protein. For example, the polynucleotide encoding the fusion protein may contain a further expression cassette from which the intermediate or "bridging" (poly)peptide(s) is/are expressed. Alternatively, the mRNA giving rise to this/these (poly)peptide(s) may be transcribed from the same promoter as the mRNA of the fusion protein, using, for example, stop/restart mechanisms well known in the art. In a further embodiment said (poly)peptide is expressed from the polynucleotide of (cb). The transposon can be combined with polynucleotides encoding the targeting fusion protein, the bridging polypeptide or the transposase (any combination of these). Alternatively, the transposable element is maintained, propagated and delivered as a separate polynucleotide molecule.

If use is made of the intermediate or "bridging" (poly) peptides and if these (poly)peptides are not encoded by any of the above recited polynucleotides, then in another preferred embodiment of the invention, said targeting system further comprises (da) a (poly)peptide comprising said DNA binding domain; and/or (db) a cellular or engineered (poly)peptide that comprises said DNA targeting domain; or (dc) at least one polynucleotide encoding said (poly)peptide of (da) and/or (db).

The targeting system of the invention may thus be comprised of a variety of components which, as a whole, guarantee the targeted insertion of the polynucleotide of interest into the desired DNA. It is understood that some of the components of the invention referred to above can be used alternatively in the targeting system of the invention. Thus, if the component denoted as (da) is present in the targeting system, then it is preferred that the domain (ii) is present in the targeting system rather than the domain denoted (i). Similarly, if the component denoted (db) is present in the system, then the domain (iv) is also present in the system rather than domain (iii), Permutations of these components are easily devisable by the skilled artisan. Thus, the fusion protein (ba) may comprise the domain (i) and the domain (iv). Then, the system would preferentially not comprise component (da). On the other hand, the system would preferentially comprise component (db). In another example, the fusion protein may comprise domain (ii) and (iii). In this case, the system would additionally require element (da) but not element (db). Instead of the elements (da) or (db), of course also corresponding element (dc) may be present in the system. As stated above, according to the guidelines given herewith, additional permutations are possible for the skilled artisan that are all comprised by the scope of the present invention.

In an additional preferred embodiment of the targeting system of the present invention, the transposon of (a) and/or the polynucleotide of (cb) and/or the polynucleotide of (bb) is comprised in one or more vectors (alternatively, the transposon may be provided without vector sequences, e.g., in circularised form).

The vector employed for any of the above recited polynucleotides may, in accordance with the present invention be an expression, a gene transfer or gene targeting vector. Expression vectors are well known in the art and widely available; see Ausubel et al., loc. cit. In this more preferred embodiment of the vector of the invention the polynucleotide is operatively linked to expression control sequences allowing expression in prokaryotic or eukaryotic cells or isolated fractions thereof. Expression of said polynucleotide(s) comprises transcription of the polynucleotide, preferably into a translatable mRNA. Regulatory elements ensuring expression in eukaryotic cells, preferably mammalian cells, are well known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers. Possible regulatory elements permitting expression in prokaryotic host cells comprise, e.g., the lac, trp or tac promoter in *E. coli*, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. Beside elements which are responsible for the initiation of transcription such regulatory elements may also comprise transcription termination signals, such as the SV40-poly-A site or the tk-poly-A site, downstream of the polynucleotide. In this context, suitable expression vectors are known in the art such as Okayama-Berg cDNA expression vector pcDV1 (Pharmacia), pCDM8, pRc/CMV, pcDNA1, pcDNA3 (Invitrogene), pSPORTI (GIBCO BRL).

Gene therapy, which is based on introducing therapeutic genes into cells by ex-vivo or in-vivo techniques is one of the most important applications of gene transfer. Suitable vectors, methods or gene-delivering systems for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813, Isner, Lancet 348 (1996), 370-374; Muhlhauser, Circ. Res. 77 (1995), 1077-1086; Onodua, Blood 91 (1998), 30-36; Verzelefti, Hum. Gene Ther. 9 (1998), 2243-2251; Verma, Nature 389 (1997), 239-242; Anderson, Nature 392 (Supp. 1998), 25-30; Wang, Gene Therapy 4 (1997), 393-400; Wang, Nature Medicine 2 (1996), 714-716; WO 94129469; WO 97/00957; U.S. Pat. Nos. 5,580,859; 5,589,466; 4,394,448 or Schaper, Current Opinion in Biotechnology 7 (1996), 635-640, and references cited therein. In particular, said vectors and/or gene delivery systems are also described in gene therapy approaches e.g. in neurological tissue/cells (see, inter alia Blömer, J. Virology 71 (1997) 6641-6649) or in the hypothalamus (see, inter alia, Geddes, Front Neuroendocrinol. 20 (1999), 296-316 or Geddes, Nat. Med. 3 (1997), 1402-1404). Further suitable gene therapy constructs for use in neurological cells/tissues are known in the art, for example in Meier (1999), J. Neuropathol. Exp. Neurol. 58, 1099-1110. The vectors used in accordance with the invention may be designed for direct introduction or for introduction via liposomes, or viral vectors (e.g. adenoviral, retroviral), for electroporation, ballistic (e.g. gene gun) or other delivery systems into the cell. Additionally, a baculoviral system can be used as eukaryotic expression system for the nucleic acid molecules of the invention. The introduction and gene therapeutic approach should, preferably, lead to the expression of a functional molecule, preferably a therapeutically active molecule, whereby said expressed molecule is particularly useful in the treatment, amelioration and/or prevention of any disease that may be ameliorated, prevented or treated by gene therapy approaches.

In a particularly preferred embodiment, at least one of said vectors is a plasmid. Plasmids are well known in the art and described for recombinant purposes, for example, in Sambrook et al, "Molecular Cloning, A Laboratory Manual", $2^{nd}$ edition, CSH Press, Cold Spring Harbor, 1989; Ausubel et al., "Current Protocols In Molecular Biology" (2001), John Wiley & Sons; N.Y. They are characterized as small extrachromosomal, usually circular double-stranded DNA molecules that replicate autonomously. They naturally occur in prokaryotes as well as eukaryotes and usually comprise at least one origin of replication and a low number of genes.

The polynucleotide of interest may be of a variety of natures. For example, it may be of non-coding nature and thus be useful in the targeted disruption of a gene that, upon overexpression, is involved in the etiology of a disease. In a further example, the transposon could contain promoter sequences that activate gene expression if the transposon inserts sufficiently close to an endogenous gene. Moreover, the transposon might lack any sequence in addition to the sequences that are required for transposition, in case a suitable selection scheme is available (e.g. one based on altered cellular phenotypes) to identify insertions into particular targets. Alternatively, the polynucleotide may be transcribed into mRNA molecules that mediate RNAi with regard to the expression of a desired target; see, for further guidance, Elbashir et al., Nature 411 (2001), 494-498, Bernstein et al., RNA 7 (2001), 1509-1521, Boutla et al., Curr. Biol. 11 (2001), 1776-1780. In a further alternative, the polynucleotide of interest serves as a sequence tag that can subsequently be used to identify the transposon insertion. The invention relates in a different preferred embodiment to a targeting system, wherein said polynucleotide of interest encodes a (poly)peptide. The gene of interest may encode markers such as the green fluorescent protein for in vivo monitoring and reporters such as luciferase or antibiotic resistance genes.

Particularly preferred is a targeting system wherein said (poly)peptide is a therapeutically active (poly)peptide. In this embodiment, (poly)peptides of therapeutic value may be targeted into cells in need of such (poly)peptides. If tissue-specific expression is desired, the tissue-specific promoters may drive expression of said (poly)peptides. The therapeutically active (poly)peptide may be any peptide or protein that counteracts the onset or progression of a disease. It may directly or indirectly interfere with said onset or progression. Therapeutically active (poly)peptides include those of the class of growth factors or differentiation factors such as GCSF, GM-CSF, as well as interleukins and interferons or engineered antibody derivatives such as scFvs that bind to adverse compounds in the body. The transposon targeting system could be used as a vector for gene therapy for monogenic diseases such as haemophilia. cDNAs, equipped with suitable transcriptional regulatory sequences, encoding blood clotting factors FactorVIII or FactorIX could be incorporated in the transposable element vector. Transposase mediates stable integration of the therapeutic genes into chromosomes, ensuring long term gene expression and an increase in of transgene products in the serum. The targeting feature could be used to direct the transposon insertion into a chromosomal location not associated with a gene, so that the insertion does not disturb endogenous gene function.

It is also preferred in accordance with the targeting system of the invention that said domains or (poly)peptides comprised in said fusion protein are joined by a linker. A "linker" is defined herein as a proteinaceous stretch of amino acids of preferably at least 6 amino acids, optionally of one or two different types of amino acids only that itself does not fulfil a biological function within a cell. The function of a linker is to tether two different (poly)peptides or domains of (poly)peptides allowing these (poly)peptides to exert the biological functions (such as binding to DNA or to a different (poly)peptides) that they would exert without being attached to said linker.

The linker may allow said domains or (poly)peptides a larger conformational freedom which may result in a better exertion of the functions assigned to said domains or (poly)peptides. The number of amino acids typically contained in linkers, preferably flexible linkers is between 5 and 20 (Crasto, C. J. and Feng, J. LINKER: a program to generate linker sequences for fusion proteins. Protein Engineering, Vol. 13, No. 5, 309-312, 2000).

Preferably, said linker is a flexible linker.

In a more preferred embodiment of the targeting system of the invention, the linker is a glycine linker or a serine-glycine linker. Chou P Y, Fasman G D. Prediction of protein conformation. Biochemistry. Jan. 15, 1994;13(2):222-45.; Ladurner A G, Fersht A R. Glutamine, alanine or glycine repeats inserted into the loop of a protein have minimal effects on stability and folding rates. J Mol Biol. Oct. 17, 1997;273(1): 330-7

The DNA targeting domain may target any DNA sequence or region that is contained within a cell. Such a region or sequence may be naturally occurring in a cell or may have artificially be introduced as is the case, for example, for transgenes or extracellularly retained DNA molecules such as plasmids. Preferred is a targeting system wherein said DNA targeting domain is a chromosomal DNA targeting domain.

In accordance with the present invention it is particularly preferred that the chromosomal DNA targeting domain is a unique chromosomal DNA sequence, a chromosomal DNA composition or a chromosomal region.

The term "a unique chromosomal DNA sequence" is a DNA sequence that occurs in eukaryotes only once per haploid genome. Examples of such unique sequences are genes or sequences within genes that occur only once within the genome such as the human genome. The term "a chromosomal DNA composition" means in accordance with the invention, a composition characterized by the percentage of bases present. An example of such a composition is an A/T rich region. Another example is a G/C rich region. The term "a chromosomal region" refers to predefined regions of the chromosome optionally characterized by higher order structures. An example of a chromosomal region is the nucleolus containing repetitive genes. A further example is a mitochondrion. It is to be understood in accordance with the invention that its underlying technical problem has also been solved if the integration site is not directly within the above referenced sequences/compositions/regions but within their vicinity such as 500 to 1000 bp or even more basepairs away, though this is less preferred. This holds particularly true if the target site is a unique sequence.

Targeting of transposition into a unique sequence could be done by artificial zinc finger peptides that can selected to specifically bind to any 18 bp DNA sequence (Beerli R R, Barbas C F 3rd. Engineering polydactyl zinc-finger transcription factors. Nat Biotechnol. February 2002;20(2):135-41.). A 18 bp sequence is likely a unique site in the human or other complex vertebrate genomes. Certain proteins are known to have high affinity to A/T-rich DNA. These include SATBI (Dickinson L A, Joh T, Kohwi Y, Kohwi-Shigematsu T. A tissue-specific MAR/SAR DNA-binding protein with unusual binding site recognition. Cell. Aug. 21, 1992;70(4): 631-45.) and SAF-A (Kipp M, Gohring F, Ostendorp T, van Drunen C M, van Driel R, Przybylski M, Fackelmayer FO. SAF-Box, a conserved protein domain that specifically recognizes scaffold attachment region DNA. Mol Cell Biol. October 2000;20(20):7480-9.), both of which interact with the nuclear matrix. Including the DNA binding domains of these protein in targeting fusion proteins is therefore expected to result in preferential transposon insertion into A/T-rich DNA. The nucleolus contains repeated regions of ribosomal RNA genes. A transposon insertion into this region therefore is not expected to be harmful to the cell. A targeting peptide that directs the transposition complex into the nucleolus could be employed. Nucleolar localization signals are known (Newmeyer DD. The nuclear pore complex and nucleocytoplasmic transport. Curr Opin Cell Biol. June 1993;5(3):395-407) and can be fused with other proteins.

Transposons and transposases derived therefrom may be of bacterial origin. However, in a further preferred embodiment of the targeting system of the present invention, the transposase or a fragment or derivative thereof having transposase function is a eukaryotic transposase or a fragment of or derived from a eukaryotic transposase. The transposase may be derived from a class I or class II transposon. As discussed herein above, the transposon is preferably a class II element.

Particularly preferred in accordance with the invention is that the transposase is or is derived from the Sleeping Beauty transposase or the Frog Prince transposase.

The Sleeping Beauty transposon and transposase are described, for example, in lzsvak et al, J. Mol. Biol. 302 (2000), 93-102. The Frog Prince transposon and transposase are described in German patent application 102 24 242.9.

In another preferred embodiment of the present invention, the targeting system comprises a fusion protein further comprising a nuclear localization signal (NLS). NLS are widely known in the art and include NLSs referred to in the appended examples. The NLSs are particularly useful in guiding the fusion proteins into the nucleus of the target cell. Alternatively, the fusion protein may additionally comprise a signal directing it into a chromosomal region such as the nucleolus (nucleolar localization signal) or to a mitochondrion. The NLS would preferably be located in the linker region connecting the two fusion partners of the fusion proteins adjacent to the linker.

The present invention relates in another preferred embodiment to a targeting system wherein said (poly)peptide(s) comprising a DNA targeting domain or said binding domain comprise(s) a dimerization domain. Many naturally occurring DNA binding/targeting proteins comprise a dimerization domain. Retainment of the dimerization domain is expected to enhance the efficiency/fidelity of the binding/targeting event; see also appended examples.

The present invention also relates to a host cell harbouring the targeting system of the invention.

The host cell of the invention may be a prokaryotic cell but is preferably a eukaryotic cell such as an insect cell such as a *Spodoptera frugiperda* cell, a yeast cell such as a *Saccharomyces cerevisiae* or *Pichia pastoris* cell, a fungal cell such as an *Aspergillus* cell or a vertebrate cell. In the latter regard, it is preferred that the cell is a mammalian cell such as a human cell. The cell may be a part of a cell line.

Also, the invention relates to a host organism comprising the host cell of the present invention. The host may be a prokaryotic or eukaryotic host and is preferably a eukaryotic host such as an insect, a yeast, a fungus, a vertebrate and preferably a mammal such as a human. The mammal is preferably a non-human mammal.

Additionally, the present invention relates to a composition comprising the targeting system of the invention. The composition may, e.g., be a diagnostic composition or a pharmaceutical composition. The various components of the composition may be packaged in one or more containers such as one or more vials. The vials may, in addition to the components, comprise preservatives or buffers for storage.

Preferably, the composition is a pharmaceutical composition.

The pharmaceutical composition composition may be in solid, liquid or gaseous form and may be, inter alia, in a form of (a) powder(s), (a) tablet(s), (a) solution(s) or (an) aerosol (s). Said composition may comprise at least two, preferably three, more preferably four, most preferably five sets of the distinct components referred to above of the invention.

It is preferred that said pharmaceutical composition, optionally comprises a pharmaceutically acceptable carrier and/or diluent. The herein disclosed pharmaceutical composition may be particularly useful for the treatment of any disease that can be prevented, alleviated or cured by means of gene therapy. Said disorders comprise, but are not limited to haemophilia, deficiency in alpha-antitrypsin, familiar hypercholesterolemia, muscular dystrophy, cystic fibrosis, cancer, severe combined immunodeficiency, diabetes, hereditary tyrosinemia type 1, and junctional epidermolysis bullosa.

Examples of suitable pharmaceutical carriers, excipients and/or diluents are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical, intradermal, intranasal or intrabronchial administration. It is particularly preferred that said administration is carried out by injection and/or delivery, e.g., to a site in muscle, liver, lung, pancreas, or solid tumors. The compositions of the invention may also be administered directly to the target site, e.g., by biolistic delivery to an external or internal target site, like the brain. The dosage regimen will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently. Proteinaceous pharmaceutically active matter may be present in amounts between 1 ng and 10 mg/kg body weight per dose; however, doses below or above this exemplary range are envisioned, especially considering the aforementioned factors. If the regimen is a continuous infusion, it should also be in the range of 1 µg to 10 mg units per kilogram of body weight per minute. A preferred dosage for the administration of DNA is $10^6$ to $10^{12}$ copies of the DNA molecule.

Progress can be monitored by periodic assessment. The compositions of the invention may be administered locally or systemically. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition of the invention may comprise further agents depending on the intended use of the pharmaceutical composition. It is particularly preferred that said pharmaceutical composition comprises further agents like immune enhancers etc.

The invention also relates to method of specifically targeting a chromosomal location comprising inserting the targeting system of the invention into a host cell.

Preferably, said insertion is effected by transfection, injection, lipofection, viral transfection or electroporation. All these insertion techniques have been widely described in the art; see literature cited above and can be adapted by the skilled artisan to the particular needs without further ado.

If an isolated cell (such as in cell culture) or a cell of a tissue outside of an organism such as a mammal is treated with the targeting system of the invention, then in an additional preferred embodiment of the method of the invention said method further comprises inserting the host cell into a host. Insertion of the host cell may be effected by infusion or injection or further means well known to the skilled artisan It is also preferred in accordance with the method of the invention that said host cell is part of a host. In this case, the insertion of the targeting system of the invention is effected in vivo. In vivo DNA delivery such as gene delivery could be accomplished by injection (either locally or systemically) of the DNA constructs. The DNA constructs can be in the form of naked DNA, DNA complexed with liposomes, PEI or other condensing agents, or can be incorporated into infectious particles (viruses or virus-like particles). DNA delivery can also be done using electroporation or with gene guns or with aerosols. Again, as discussed herein above, when inserting the targeting system of the invention into the host cell or host, some of the components may already be comprised in the host cell or host which would be regarded as a transgenic host cell or host (although the components might be retained extrachromosomally) when the missing components for completion of the system are introduced.

The figures show:

FIG. 1. Experimental strategy for transposon targeting using fusion proteins in which one partner is a protein that binds to a specific DNA sequence within the transposable element. The components of the targeting system include a transposable element that minimally contains the terminal inverted repeats containing the transposase binding sites (arrowheads), and may contain a gene of interest equipped with a suitable promoter. Targeting is achieved by a fusion protein in which one partner is a protein that binds to a specific DNA sequence within the transposable element (anchor domain), whereas the other partner is responsible for targeting. In this strategy, the transposase is not modified. (A) a fusion protein in which a specific DNA-targeting protein domain, responsible for binding to the target DNA, is fused to the anchor domain, thereby rendering a novel, and sequence-specific DNA-binding/targeting function to it; (B) a fusion protein in which a protein domain interacts with an endogenous or engineered DNA-targeting protein; (C) a fusion protein in which a nucleolar localization signal directs the transposition complex into the nucleolus, which is composed of repetitive ribosomal RNA genes.

FIG. 2. Transposon targeting into chromosomal scaffold attachment regions. (A) (SEQ ID NOs: 1 and 2) Components of a targeting system for transposon insertion into scaffold attachment regions (SARs). The targeting fusion protein consists of the bacterial LexA DNA-binding protein, a nuclear localization signal (NLS) which is responsible for directing the fusion protein into the nucleus, and the SAF-box which is a DNA-binding domain of the human SAF-A protein, one of the proteins known to bind to SARs. A control protein lacks the SAF-box. The transposable element contains a 16-bp binding site for the LexA protein between the left inverted repeat of the transposon and the SV40 promoter that drives expression of the zeocin resistance gene. (B) Transposition of the element shown above, in human HeLa cells, in the presence or absence of the targeting fusion protein.

FIG. 3. Preferential insertion into SARs by transposon targeting. Transposition events were recovered from transformed cells, and human chromosomal DNA flanking the insertion sites was analyzed with respect to proximity to chromosomal SARs (or MARs). The MAR-Wiz program was used to predict the presence of a SAR in the vicinity of a transposon insertion. Distances were categorized, and the numbers of insertions obtained in the presence and in the absence of the targeting fusion protein in each category are shown.

FIG. 5. In vitro binding of SB target sites by the SAF box. Radioactively labeled transposon target sites were incubated with a SAF box peptide bound to resin, and radioactivity retained on the resin after extensive washing was measured.

Two out of three samples show considerable binding compared to the negative control (bacterial plasmid DNA).

FIG. 6. Transposon targeting into the tetracycline response element (A) Components of a targeting system for transposon insertion into the tetracycline response element (TRE). The targeting fusion protein consists of the tetracycline repressor, a bacterial DNA-binding protein binding to the TRE, a nuclear localization signal (NLS) which is responsible for directing the fusion protein into the nucleus, and the bacterial LexA DNA-binding protein, that binds to the 16-bp binding site in the transposable element. Two versions were made: one that contains only the DNA-binding domain (DBD) of the LexA protein, and the other containing the full-length (FL) LexA protein. The target DNA in this experiment is a chromosomally integrated TRE sequence upstream of the CMV minimal promoter and the EGFP gene, in human HeLa cells. (B) Mobility shift experiment showing the ability of the targeting fusion protein containing the full-length LexA protein to specifically bind to radiolabeled TRE and transposon probes.

FIG. 7. Targeted transposition into the CMV minimal promoter in the proximity of the TRE chromosomal target. (A) Components of the experimental system include the transposable element with the LexA binding site between the left inverted repeat of the transposon and the SV40 promoter driving the expression of a zeocin resistance gene, the targeting fusion protein containing the full-length LexA protein, the transposase, and the TRE-CMV-EGFP target which had been preintegarted into human chromosomal DNA. (B) (SEQ ID NO.: 3) Targeted transposition close to the TRE. Two transposon insertions were recovered that occurred in the close proximity of the TRE region, within two TA dinucleotides of the CMV promoter TATA-box.

The examples illustrate the invention.

The Sequence Listing submitted herewith in computer readable form is incorporated herein by reference.

REFERENCE EXAMPLE 1

Tagging the SB Transposase with Histidine-Tags

Histidine-tags were fused N-terminally and C-terminally to the Sleeping Beauty transposase by recombinant means. An N-terminal fusion completely abolished transposition activity, whereas a C-terminal tag reduced transposition activity to about 5-10% in vivo. Apparently, the SB transposase did not tolerate these additions, possibly due to an effect on protein folding. The N-terminal region of SB transposase contains two helix-turn-helix (HTH) domains responsible for specific binding of the transposase to the transposon inverted repeats. The function of the C-terminus is unknown, but this region of the protein is predicted to have a helical structure. C-terminal protein association determinants are present in different recombinases. For example, the crystal structure of Tn5 transposase, which acts as a dimer, shows that the main dimerization surface is provided by the C-terminus. The C-terminal regions of retroviral integrases were also found to encode multimerization functions. Taken together, it appears that protein tags interfere with transposition by compromising certain functions of the transposase, including DNA-binding and dimerization. We therefore concentrated our efforts to investigate possibilities of transposon targeting by using specifically designed targeting fusion proteins.

EXAMPLE 1

Figure 2A:
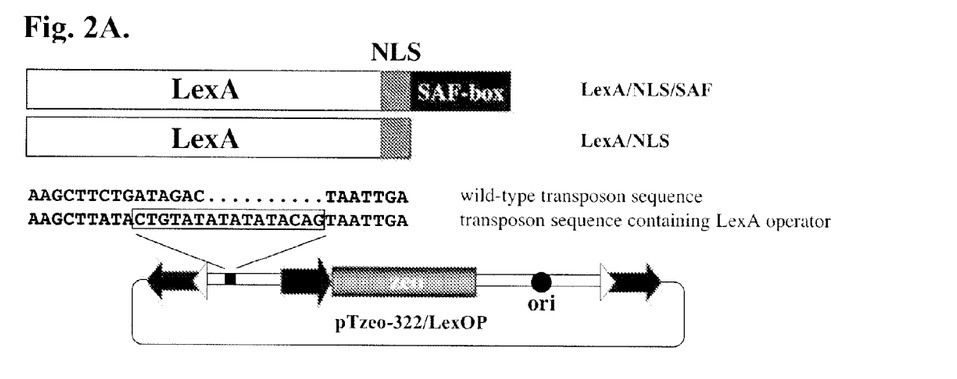

Targeted Sleeping Beauty Transposition into Chromosomal Scaffold Attachment Regions in Cultured Human Cells Because the efficiency of transposon targeting was a priori unknown, we began our experiments with targeting into chromosomal regions that are represented many times in a complex genome, whose base composition is AT-rich so that SB can efficiently integrate into them, and for which interacting protein determinants were known and well characterized. Scaffold attachment regions (SARs), also called matrix attachment regions or MARs, that partition the genome into distinct, independent loops by binding to the nuclear matrix satisfy the above criteria. Scaffold attachment factor A (SAF-A) is one of several proteins known to bind to SAR DNA. SAF-A contains an evolutionarily conserved protein domain, termed the SAF-box, which is necessary and sufficient to mediate SAR binding. We have engineered a fusion protein in which the N-terminal 45 amino acids of SAF-A, containing the SAF-box, was fused to the C-terminus of the *E. coli* LexA protein (FIG. 2A). The fusion protein also contained the nuclear localization signal (NLS) of the SV40 T antigen to ensure efficient transport of the targeting protein into the nuclei of cells, where transposition should occur. The function of the LexA protein in this experimental approach is to specify binding of the targeting fusion protein to a LexA operator site, engineered into an SB transposon vector (FIG. 2A). LexA is a protein foreign to a human cell, and the 16-bp LexA operator sequence (FIG. 2A) is most likely absent in the human genome; thus, expression of the targeting fusion protein is unlikely to interfere with endogenous gene activity. The LexA operator site was placed between the left inverted repeat of SB and an SV40 enhancer/promoter element driving the expression of a zeocin (zeo) antibiotic resistance gene within the transposon (pTzeo-322/LexOP in FIG. 2A). We chose this region of the transposon for the operator site in the hope that binding of the targeting protein would not interfere with either transposition or transgene expression. We hypothesized that targeted transposition would occur by simulteneous interaction of the fusion protein with both the transposon vector and chromosomal SAR regions, thereby forcing the transposition complex to integrate into nearby sites.

Figure 2B:
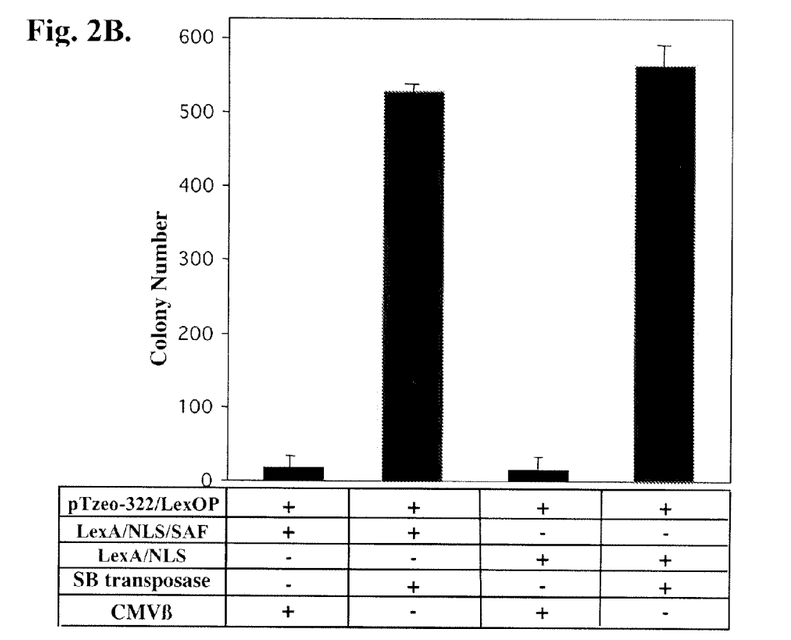

First, the effect of expression of the targeting protein on SB transposition was examined by comparing transpositional efficiencies in human HeLa cells transfected with a plasmid expressing the SB transposase (pCMVWSB), pTzeo-322/LexOP and a plasmid either expressing the LexA/NLS/SAF fusion or LexA/NLS only (FIG. 2A). No difference in transpositional activity was observed (FIG. 2B), indicating that binding of the fusion protein to the transposon does not interfere with transposition.

Next we asked whether targeted transposition into SAR DNA can occur. HeLa cells were cotransfected and placed under zeocin selection as above. In the absence of suitable methods for directly selecting transposition events in SARs, cells were pooled, and SB integration sites were cloned out from genomic DNA by plasmid rescue, taking advantage of the plasmid origin of replication inside the element (FIG. 2A). Genomic DNA flanking the inserted transposons were sequenced and analyzed using a computer software called MAR-Wiz, available on futuresoft.org, which was developed for the purpose of discovering the presence of MARs within DNA sequences. MAR-Wiz predicts MARs based on the co-occurrence of DNA sequence patterns and structural features, such as AT-richness, bendability, and presence of topoisomerase 11 recognition sites, that have been shown to occur in the neighborhood of MARs. The mathematical density of the occurrences of these features in a DNA region is assumed to imply the presence of a MAR in that region.

Figure 3:
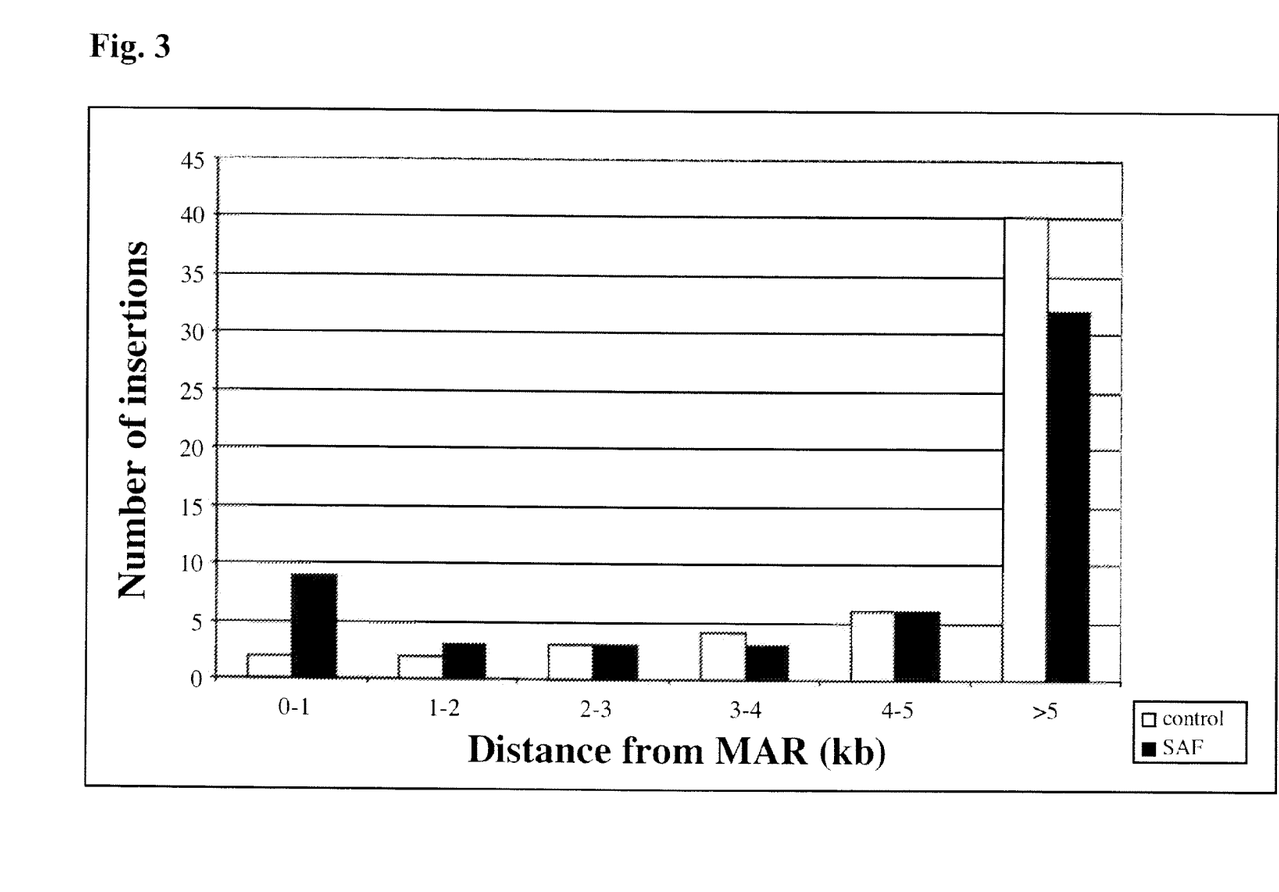
Figure 4:
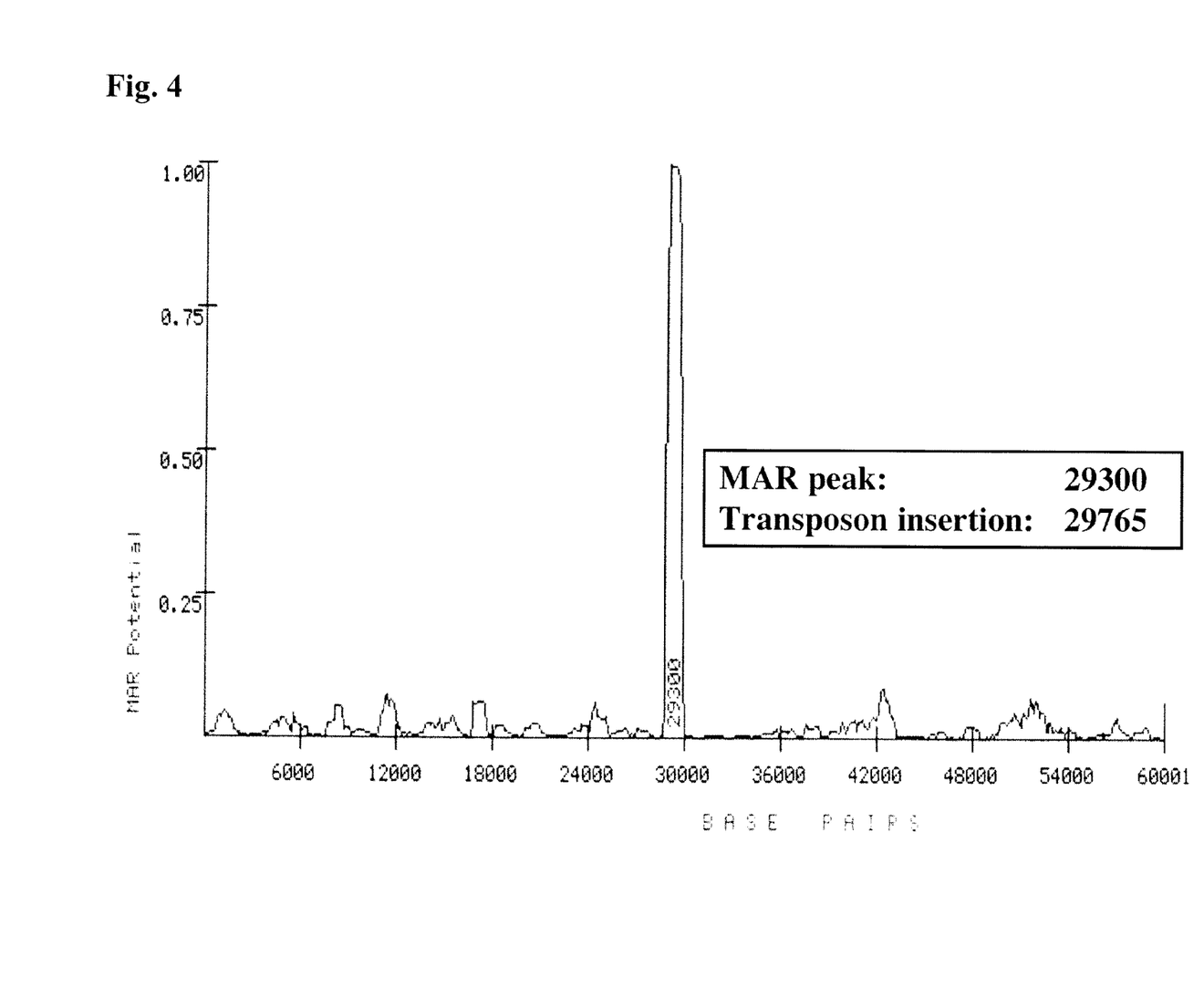
FIG. 4. MAR-Wiz output showing the position of a predicted SAR (MAR). A transposon insertion close to this MAR is shown.

We have analyzed 56 unique SB insertions recovered from cells expressing the LexA/NLS/SAF targeting fusion protein and 57 from cells expressing LexA/NLS only. The proximity of each insertion site to a predicted MAR was calculated with the MAR-Wiz program, and the distances categorized into six groups (FIG. 3). As shown in FIG. 3, the most notable difference between the two data sets are in the group of insertions that are the closest to a MAR. Specifically, 9 insertions in the targeting group occurred within 1 kb distance from a predicted MAR versus 2 events in the control group. An output of the MAR-Wiz program showing the positions of the MAR peak and the transposon insertions is shown in FIG. 4. Our results indicate a shift in the insertional spectrum of SB in the presence of the targeting fusion protein, and indicate that in the presence of the targeting fusion protein more insertions occurred in the vicinity of genomic MAR sequences.

Some of the chromosomal DNA fragments predicted to contain MAR sequences in close proximity of the SB target sites by computer analysis (MAR-Wiz) were tested in an in vitro assay for binding by the SAF-A protein. The ZZ-45 protein is a recombinant SAF-A peptide expressed as a C-terminal fusion to an artificial double-Z domain tag (tandem of the IgG-binding domain of Protein A). The protein is purified using affinity chromatography against the tag similarly as described in Gohring et al. (1997) EMBO K. 16:7361-7371.

A DNA-binding assay similar to Kipp et al (MCB 20(20): 7480-7489) was used to test whether DNA fragments are bound specifically by the SAF-domain. The SAF domain peptide was immobilized on the IgG resin. The DNA fragments to be tested and the control DNAs were radioactively labelled. Positive control is pMII human DNA effectively bound by SAF-A (Kipp et al., 2000). Bacterial plasmid DNA served as the negative control.

Figure 5:
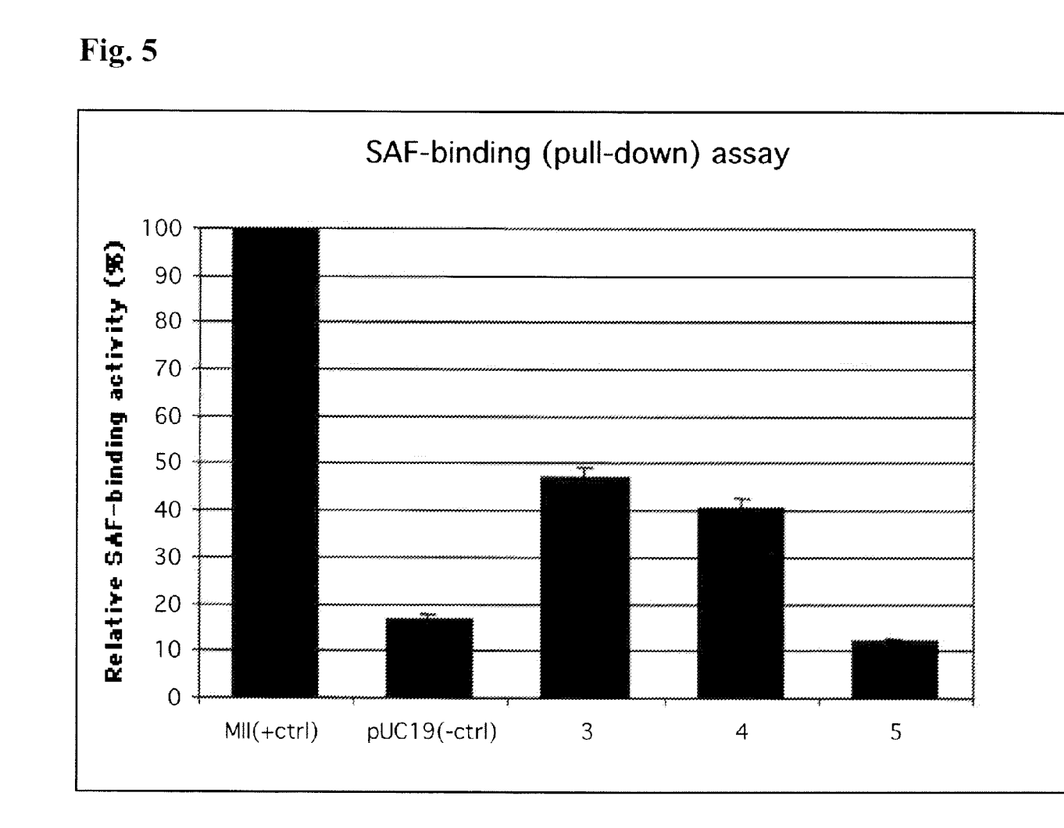

The labelled DNA fragments were incubated together with the immobilized SAF-binding peptide in binding buffer. Sheared *Escherichia coli* DNA was added to the binding reactions as an unlabelled unspecific competitor in 1000-fold excess. Unbound DNA was removed by washing the complex extensively with the binding buffer. DNA binding was quantified by scintillation counting. DNA samples were tested when the assay was reproducibly functioning with the controls. As shown in FIG. 5, two out of the three SB target sites tested showed considerable binding to the SAF box peptide. This result strengthens the explanation that these SB insertions were indeed targeted to MAR regions by the targeting fusion protein containing the SAF box.

EXAMPLE 2

Figure 6A:
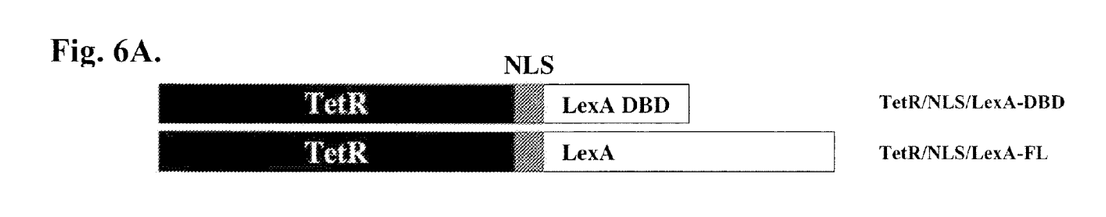

Targeted Sleeping Beauty Transposition into a Unique Chromosomal Site in Human Cells Encouraged by the above results, we next sought evidence for targeted transposition into a unique site in the human genome. For this purpose, we concentrated our efforts to the tetracycline repressor-operator system, widely used in the Tet-On/Tet-Off regulatable gene expression vectors. Unlike binding of the SAF-box to scaffold attachment regions, interaction of the tetracycline repressor with its operator site is highly sequence-specific. We have generated a transgenic, HeLa-derived cell line containing a tetracycline response element (TRE)-driven EGFP gene, which serves as a chromosomal target for transposon integration (FIG. 6A). The targeting fusion protein consisted of the tetracycline repressor, an NLS and the LexA protein (FIG. 6A). The transposon vector was pTzeo-322/LexOP, as above. As previously, our hypothesis was that targeted transposition into, or close to the TRE could occur via interaction of the fusion protein with both the transposon vector and the TRE.

Figure 6B:
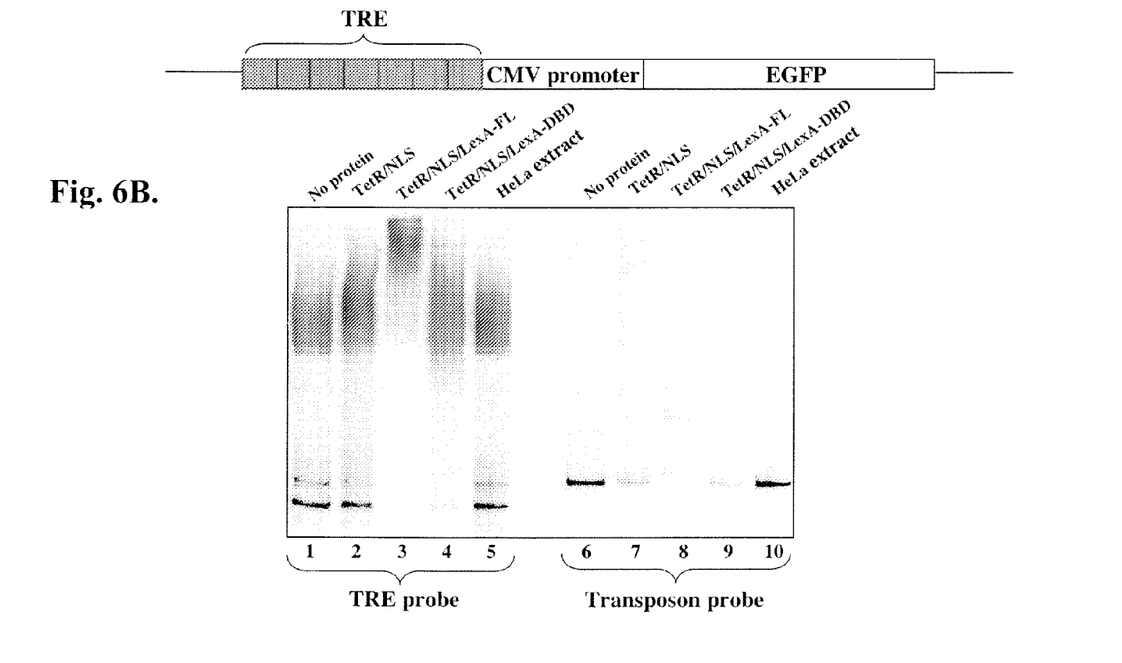

First, we tested the relative efficiencies of two fusion proteins for binding to the TRE and the LexA operator-containing transposon. One of the proteins contained only the N-terminal 87 amino acids encoding the DNA-binding domain of the LexA protein fused to the tetracycline repressor (TetR/NLS/LexA-DBD in FIG. 6A), whereas the other contained the complete LexA protein (TetR/NLS/LexA-FL in FIG. 6A). The reason we wanted to test this is that both the tetracycline repressor and the LexA proteins bind to their binding sites as dimers, and it was of interest to test whether the combination of two dimerization domains in the fusion protein would affect DNA-binding. An electrophoretic mobility shift experiment was done using nuclear extracts of HeLa cells transfected with the fusion protein expression constructs and radioactively labeled TRE and transposon probes (FIG. 6B). Both the TRE and the transposon probes were shifted with TetR/NLS/LexA-FL (FIG. 6B, lanes 3 and 8), but not with TetR/NLS/LexA-DBD (FIG. 6B, lanes 4 and 9) or with TetR/NLS (FIG. 6B, lanes 2 and 7) or with a nuclear extract prepared from untransfected cells (FIG. 6B, lanes 5 and 10). This result shows that the C-terminal dimerization domain of LexA is required for efficient, sequence-specific DNA-binding of the fusion protein to both the teracycline and LexA operator sites. Similar observations were made for retrovirus integrase-LexA fusion proteins, and for other fusions with LexA; namely, the C-terminal dimerization domain of LexA is required for efficient DNA-binding. We confirmed our results in vivo, by coexpression of TetR/NLS/LexA-FL or TetR/NLS/LexA-DBD together with the tetracycline transactivator in HeLa cells transgenic for TRE-EGFP. The higher affinity a targeting fusion protein has to the TRE, the higher repression effect it will have on EGFP expression, presumably because it will compete for TRE binding with the tetracycline transactivator. In the positive control, only the tetracycline transactivator was transfected. TetR/NLS/LexA-FL reduced the number of EGFP-positive cells to about 50% of the positive control, whereas TetR/NLS/LexA-DBD did not appreciably influence EGFP expression (data not shown). TetR/NLS/LexA-FL was therefore used in subsequent experiments to demonstrate targeted SB transposition into the TRE.

Figure 7A:
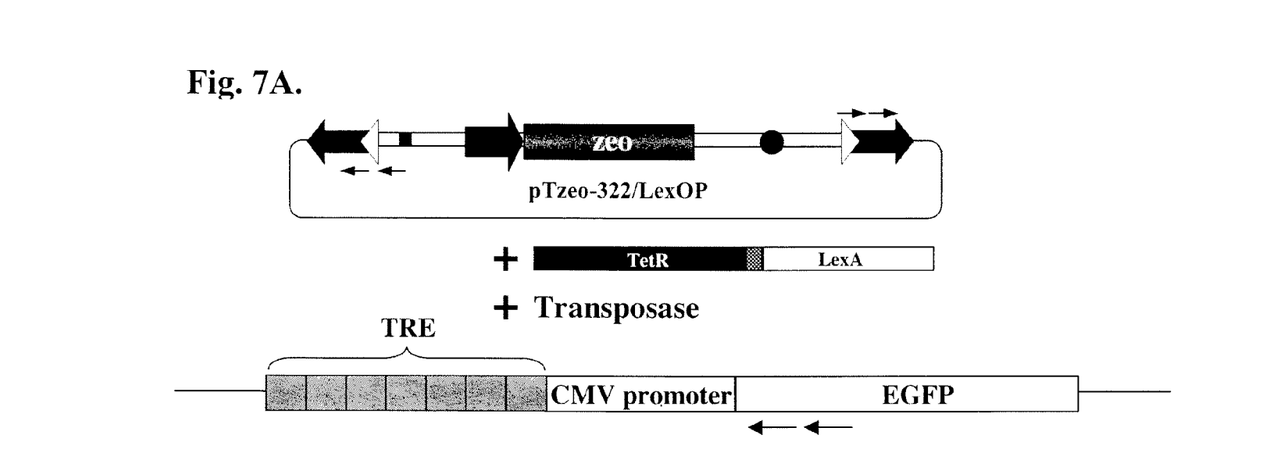
Figure 7B:
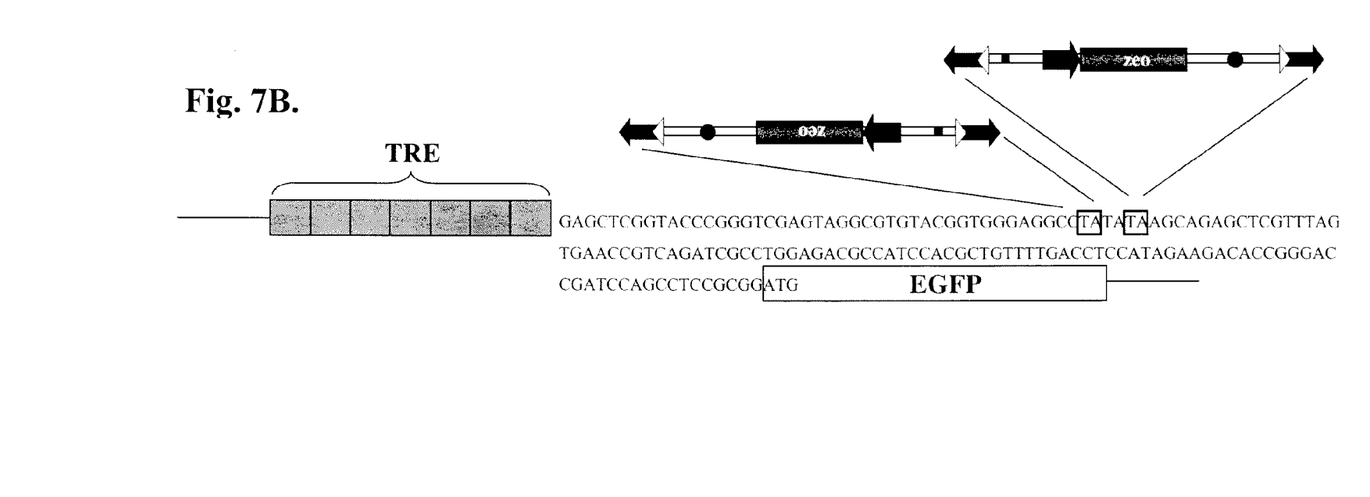

The TRE-EGFP transgenic cell line was cotransfected with pCMV/SB, pTzeo-322/LexOP and TetR/NLS/LexA-FL. After two weeks of selection with zeocin, approximately 400 cell colonies were pooled, genomic DNA prepared and subjected to PCR analysis with primers designed to amplify transposition events upstream of the EGFP gene (FIG. 7A). PCR products consistent with transposon integration in both orientation with respect to the EGFP gene were obtained, and cloned into plasmid vectors. Sequencing of the PCR products revealed transposition of SB in the two different possible orientations into two TA sites in the promoter region of the EGFP gene, 44 and 48 bps downstream of the TRE region (FIG. 7B). These TA sites are part of the TATA-box of the CMV minimal promoter. Because PCR will not differentiate between integration events into the same site, we calculate that the efficiency of transposon targeting in this experiment was at least two events per 400 transposition events in total. In conclusion, our targeting fusion protein is active in directing targeted SB element transposition into the vicinity of a specific DNA sequence in the human genome. Our results represent the first in vivo demonstration of targeted transposition of an otherwise relatively randomly integrating element in cells of higher vertebrates.

(c) a third vector comprising a polynucleotide encoding a transposase or a fragment or derivative thereof having transposase function.

The invention claimed is:

1. A targeting system comprising
   (a) a first vector comprising a transposon which is devoid of a polynucleotide encoding a functional transposase comprising
      (aa) a polynucleotide of interest; and
      (ab) a DNA sequence specifically recognized by a DNA binding domain, wherein the DNA sequence does not have inverted repeats of a transposon; and
   (b) a second vector comprising a polynucleotide encoding a fusion protein, wherein the fusion protein nor the components recited in (i)-(iv) do not directly mediate integration of a transposon, comprising
      (i) said DNA binding domain; or
      (ii) a (poly)peptide binding domain binding to a (poly)peptide comprising said DNA binding domain; and
      (iii) a DNA targeting domain; or
      (iv) a (poly)peptide binding domain that binds to a cellular or engineered (poly)peptide that comprises a DNA targeting domain; and 2. The targeting system of claim 1 wherein the polynucleotide of (b) further encodes at least one (poly)peptide as described in (ii) or (iv).

3. The targeting system of claim 1 further comprising
   (da) a (poly)peptide comprising said DNA binding domain; and/or
   (db) a cellular or engineered (poly)peptide that comprises said DNA targeting domain; or
   (dc) at least one polynucleotide encoding said (poly)peptide of (da) and/or (db).

4. The targeting system of claim 1 wherein at least one of said vectors is a plasmid.

5. The targeting system of claim 1 wherein said polynucleotide of interest encodes a (poly)peptide.

6. The targeting system of claim 5 wherein said (poly)peptide is a therapeutically active (poly)peptide.

7. The targeting system of claim 1 wherein said domains or (poly)peptides comprised in said fusion protein are joined by a linker.

8. The targeting system of claim 7 wherein said linker is a flexible linker.

9. The targeting system of claim 1 wherein the linker is a glycine linker or a serine-glycine linker.

10. The targeting system of claim 1 wherein said DNA targeting domain is a chromosomal DNA targeting domain.

11. The targeting system of claim 10 wherein the chromosomal DNA targeting domain is a unique chromosomal DNA sequence, a chromosomal DNA composition or a chromosomal region.

12. The targeting system of claim 1 wherein the transposase or a fragment or derivative thereof having transposase function is a eukaryotic transposase or a fragment of or derived from a eukaryotic transposase.

13. The targeting system of claim 12 wherein the transposase is or is derived from the Sleeping Beauty transposase or the Frog Prince transposase.

14. The targeting system of claim 1 wherein the fusion protein further comprises a nuclear localization signal (NSL).

15. The targeting system of claim 1 wherein said poly) peptide(s) comprising said DNA targeting domain or said binding domain comprise(s) a dimerization domain.

16. A host cell harbouring the targeting system of claim 1.

17. A composition comprising the targeting system of claim 1.

18. The composition claim 17 which is a pharmaceutical composition.

19. An in vitro method of specifically targeting a chromosomal location comprising inserting the targeting system of claim 1 into a host cell in vitro.

20. The method of claim 19 wherein said insertion is effected by transfection, injection, lipofection, viral transfection or electroporation.

* * * * *

SEQUENCE LISTING

```
<160> NUMBER OF SEQ ID NOS: 3

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence: Wild-type
      transposon sequence
<220> FEATURE:
<221> NAME/KEY: misc_feature
<222> LOCATION: (16)..(25)
<223> OTHER INFORMATION: n is a, c, g, or t

<400> SEQUENCE: 1
aagcttctga tagacnnnnn nnnnntaatt ga                                    32

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Transposon
      sequence containing LexA operator

<400> SEQUENCE: 2
aagcttatac tgtatatata tacagtaatt ga                                    32

<210> SEQ ID NO 3
<211> LENGTH: 150
<212> TYPE: DNA
<213> ORGANISM: Artificial Sequence
<220> FEATURE:
<223> OTHER INFORMATION: Description of Artificial Sequence: Segment of
      target sequence of plasmid pTRE-d2EGFP

<400> SEQUENCE: 3
gagctcggta cccgggtcga gtaggcgtgt acggtgggag gcctatataa gcagagctcg      60
tttagtgaac cgtcagatcg cctggagacg ccatccacgc tgttttgacc tccatagaag    120
acaccgggac cgatccagcc tccgcggatg                                     150
```